United States Patent
Foster et al.

(10) Patent No.: US 6,803,061 B1
(45) Date of Patent: Oct. 12, 2004

(54) INGESTIBLE CHEWING GUM FOR ANIMALS

(75) Inventors: John W. Foster, Piscataway, NJ (US); Weisheng Li, Bridgewater, NJ (US); Jingping Liu, Highland Park, NJ (US); Leonard Haring, Jr., Jackson, NJ (US)

(73) Assignee: Wm. Wrigley Jr. Company, Chicago, IL (US)

( * ) Notice: Subject to any disclaimer, the term of this patent is extended or adjusted under 35 U.S.C. 154(b) by 262 days.

(21) Appl. No.: 09/632,840

(22) Filed: Aug. 4, 2000

Related U.S. Application Data

(60) Provisional application No. 60/148,045, filed on Aug. 4, 1999.

(51) Int. Cl.$^7$ .............................. A23G 3/30; A23K 1/18
(52) U.S. Cl. ................. 426/2; 426/3; 426/805
(58) Field of Search ............................... 426/3, 2, 805; 424/440

(56) References Cited

U.S. PATENT DOCUMENTS

| 4,087,557 A | 5/1978 | Bakal et al. ................... 426/3 |
| 4,765,991 A | 8/1988 | Cherukuri et al. ............. 426/3 |
| 4,780,324 A | 10/1988 | Knebl et al. .................... 426/3 |
| 4,980,177 A | 12/1990 | Cherukuri et al. ............. 426/3 |
| 5,366,740 A | 11/1994 | Shaw et al. ..................... 426/3 |
| 5,482,722 A | 1/1996 | Cook ............................. 426/3 |
| 5,580,590 A | 12/1996 | Hartman ........................ 426/3 |
| 5,882,702 A | 3/1999 | Abdel-Malik et al. ......... 426/3 |

FOREIGN PATENT DOCUMENTS

| WO | 98/58550 | 12/1998 |
| WO | 99/39588 | 8/1999 |
| WO | 00/19837 | 4/2000 |

*Primary Examiner*—Arthur L. Corbin

(57) ABSTRACT

An animal digestible chewing gum composition is provided comprising a water soluble gum portion and water insoluble gum base portion including an animal digestible elastomer. Additionally, a method for creating an animal digestible chew gum is provided comprising the steps of creating a chewing gum base that includes a sufficient amount of an animal digestible elastomer to create a resultant chewing gum that is more digestible by an animal than a chewing gum without such an elastomer, and adding to the chewing gum base a water soluble portion to create a resultant chewing gum.

11 Claims, No Drawings

INGESTIBLE CHEWING GUM FOR ANIMALS

This application claims priority to provisional application Ser. No. 60/148,045 filed Aug. 4, 1999.

BACKGROUND OF THE INVENTION

The present invention relates generally to chewing gum compositions and methods of making the same. More specifically, the present invention relates to chewing gum compositions capable of being chewed and ingested by animals.

For hundreds of years, people have enjoyed gum-like substances. In the late 1800's the predecessors to today's chewing gum compositions were developed. Today, chewing gum is enjoyed daily by millions of people world-wide.

However, such currently available chewing gum compositions suitable for humans are not suitable for animals. Animals, including, but not limited to, cats and dogs are not capable of chewing currently available chewing gum compositions for an extended period of time. When animals are fed such prior art chewing gum compositions, they frequently bite and immediately swallow the gum as if it were food.

Further, pet owners are constantly challenged to maintain their pet's dental hygiene. Prior art studies of humans have shown that chewing gum between meals provides positive dental health benefits. Such human-based prior art gum compositions clean teeth through mechanical cleansing and stimulation of salivary flow. Yet, since prior art human-based gum compositions are not capable of being ingested by animals, such compositions are not suitable for animals. Thus, pet owners are without the benefit of a chewing gum composition for animals, which could provide dental hygiene benefits.

In addition, there is a concern in the pet community, in particular for dogs, that currently available common natural dog treats such as rawhide, pigs ears, and the like contain parasites and toxic microorganisms. Recent prior art studies have shown that Salmonella problems for animals appear to be associated with rawhide based animal treats.

Therefore, there is a need within the prior art for an ingestible chewing gum for animals, which is capable of being chewed over an extended period of time before being ingested. There is also a need for an animal ingestible chewing gum composition, which is substantially free of parasites and toxic microorganisms unlike rawhide prior art based compositions.

Lastly, there is also a need for a method of making an animal ingestible chewing gum composition capable of extending the period of time an animal chews such a composition before swallowing, and which is also substantially free of parasites and toxic microorganisms.

SUMMARY OF THE INVENTION

The present invention provides for an animal ingestible chewing gum composition, which is capable of extending the period of time an animal chews such a composition before swallowing, and method of making the same. Further, the chewing gum composition of the present invention is also capable of being substantially free of parasites and toxic microorganisms.

To this end, the present invention provides for an animal ingestible chewing gum composition and method of making the same through use of at least one animal-protein, plant-protein, or polysaccharide-based elastomer alone or in combination with one another. These animal-ingestible elastomers provide a chewing gum composition capable of being chewed over an extended period of time by an animal prior to ingestion. In addition, such elastomers also are substantially free of parasites and toxic microorganisms, thereby increasing the animal health safety profile of the chewing gum composition.

Accordingly, a chewing gum composition is provided that comprises a water soluble gum portion and water insoluble gum base portion including at least one animal-protein, plant-protein, or polysaccharide-based elastomer alone or in combination that may dissolve or may be water insoluble.

In an embodiment, the gum base of the present invention may comprise from approximately 1% to about 99% by weight of at least one animal-protein, plant-protein, or polysaccharide-based animal ingestible elastomer.

In an embodiment, the animal-protein, plant-protein, or polysaccharide-based animal ingestible elastomer is coupled to a medicament.

In an embodiment, the animal-protein, plant-protein, or polysaccharide-based animal ingestible elastomer is coupled to a nutritional compound.

In an embodiment, the animal-protein, plant-protein, or polysaccharide-based animal ingestible elastomer is coupled to a breath-freshening ingredient.

In an embodiment, the gum base may also include other zoologically acceptable elastomers.

In an embodiment, the gum base may also include a zoologically acceptable elastomer plasticizer.

The present invention also provides a method for creating an animal ingestible chewing gum composition, which is capable of extending the period of time the animal chews the composition before ingestion comprising the steps of: creating a chewing gum base that includes a sufficient amount of at least one animal-protein, plant-protein, or polysaccharide-based animal ingestible elastomer alone or in combination to create a resultant chewing gum that is more digestibly acceptable to and extends the period of chewing for an animal than a chewing gum composition without such animal-protein, plant-protein, or polysaccharide-based animal ingestible elastomers; and adding the chewing gum base to a water soluble portion to create a resultant chewing gum. Further, the method provides for the creation of an animal digestible chewing gum composition that is substantially free of parasites and toxic microorganisms unlike natural rawhide based animal ingestible products.

In another embodiment, the present invention provides a chewing gum composition comprising a flavor, a sweetener, a texturizer, and at least one animal-protein, plant-protein or polysaccharide-based animal ingestible elastomer that is capable of extending the period of time the animal chews such a composition before ingestion.

An advantage of the present invention is to provide an animal ingestible chewing gum composition that is capable of extending the period of time an animal chews such a composition before ingestion. In doing so, the animal receives a variety of masticatory benefits such as improved dental hygiene through enhanced mechanical cleansing and salivary flow.

Another advantage of the present invention is to provide a chewing gum base that contains at least animal-protein, plant-protein, or polysaccharide-based elastomer capable of being ingested by an animal.

Furthermore, an advantage of the present invention is to provide a chewing gum composition containing an animal-protein, plant-protein, or polysaccharide-based animal ingestible elastomer substantially free of parasites and/or toxic microorganisms unlike natural rawhide animal chew products. In doing so, the present invention provides enhanced animal health safety.

Moreover, an advantage of the present invention is to provide a chewing gum composition containing at least animal-protein, plant-protein or polysaccharide-based animal ingestible elastomer alone or in combination that can be attached to any one or more currently available elastomers, medicaments, nutritional compounds, or breath-freshening agents for delivery to the animal via chewing the gum and/or swallowing the gum cud.

Moreover, an additional advantage of the present invention is to provide a method for producing an animal ingestible chewing gum composition containing at least one animal-protein, plant-protein or polysaccharide-based animal ingestible elastomer alone or in combination with one another, which is capable of extending the period of time an animal chews the composition before ingestion.

Additional features and advantages of the present invention are described herein, and will be apparent from, the detailed description of the presently preferred embodiments.

DETAILED DESCRIPTION OF THE PRESENTLY PREFERRED EMBODIMENTS

The present invention provides an animal chewing gum composition and method for making the same. Pursuant to the present invention, animal ingestible chewing gum composition is provided and includes at least one animal-protein, plant-protein or polysaccharide-based animal ingestible elastomer alone or in combination, which are capable of extending the period of time the animal chews the composition prior to ingestion. Further, the chewing gum composition of the present invention may be substantially free of parasites and/or toxic microorganisms. Through extended animal chewing created by such an animal ingestible chewing gum medicinal and nutritional composition, compounds may be attached to the composition of the present invention and subsequently delivered to the animal.

Typical chewing gum ingredients include: elastomers; elastomer plasticizers; fillers; softeners; waxes, antioxidants; colorants; flavors; sweeteners; high intensity sweeteners; flavoring agents, softeners, emulsifiers; colors, acidulants; and other components that provide desirable attributes to the animal chewing gum composition.

Chewing gum generally consists of a water insoluble gum base portion, a water soluble portion, and flavors, medicaments, or nutritional compounds. The water soluble portion dissipates with a portion of the flavor, medicament, or nutritional compound over a period of time during chewing. The gum base portion is retained in the mouth throughout the chew. The insoluble gum base generally comprises of elastomers, resins, fats and oils, softeners and inorganic fillers.

Elastomers provide the rubbery, cohesive nature to the gum, which varies depending on the ingredient's chemical structure and how it is blended with other ingredients. It has been surprisingly discovered that certain food-proteins and polysaccharides are ingestibly safe for animals and capable of extending the time an animal chews compositions containing such ingredients. Further, it has been surprisingly discovered that these certain food proteins and polysaccharides are substantially free of parasites and/or toxic microorganisms. Such novel animal digestible food-proteins and polysaccharides includes certain animal-protein, plant-protein or polysaccharide-based elastomers which may be used alone or in combination with one another in the preferred embodiments of the present invention. Examples of animal digestible animal-protein elastomers of the preferred embodiment include, but are not limited to, casein, caseinate, gelatin, whey protein, combinations thereof and derivatives thereof.

Examples of animal digestible plant-protein elastomers of the preferred embodiment include, but are not limited to, gliadin, gluten, glutenin, soya protein, zein, barley protein, combinations thereof and deritives thereof.

Examples of animal digestible polysaccharide-based elastomers of the preferred embodiment include, but are not limited to, agar, carrageenan, cellulose, corn syrup, guar gum, gum arabic, gum karaya, gum tragacanth, konjac gum, pectin, pullulan, starch, xanthan gum, gellan gum, combinations thereof, and derivatives thereof.

Preferred animal digestible elastomers of the preferred embodiment include wheat, gliadin, wheat gluten, zein, combinations thereof, and derivatives thereof. In addition, any of the animal digestible elastomers of the present invention may be used in combination with one another as well.

In addition to the animal digestible elastomer of the preferred embodiment, other currently available elastomers may be used within with the ingredient make-up of the preferred embodiment. Traditional elastomers suitable for use within the gum base of the preferred embodiment include: natural rubber such as smoked or liquid latex and guayule, natural gums such as jelutong, lechi caspi perillo, massaranduba balata, massaranduba chocolate, nispero, rosidinha, chicle, gutta percha, gutta kataiu, niger gutta, tunu, chilte, chiquibul, gutta hang kang, synthetic rubber such as butadiene-styrene copolymers, polyisobutylene, isobutylene-isoprene copolymers, polyethylene, vinyl copolymers such as vinyl acetate/vinyl laurate, ethylene/vinyl acetate, polyvinyl alcohol mixtures thereof, and derivatives thereof.

Elastomer plasticizers vary the firmness of the gum base. Their polymer plasticizing strength and their varying softening points cause varying degrees of finished gum firmness when used in the gum base. This is an important consideration when one wants to use flavorants that differ in plasticizing strength for the gum base in the finished gum.

Elastomer plasticizers suitable for use within the gum base of the preferred embodiment include, but are not limited to, natural rosin esters such as gycerol ester of partially hydrogenated rosin, glycerol ester of polymerized rosin, glycerol ester of partially dimerized rosin, glycerol ester of rosin, glycerol ester of tall cil rosin, pentaerythritol esters of partially hydrogenated rosin, partially hydrogenated methyl esters of rosin, pentaerythritol ester of rosin, synthetic elastomer plasticizers such as terpene resins derived from alpha-pinene, beta-pinene and/or d-limonene mixtures thereof, and derivatives thereof.

Fillers modify the texture of the base and aid in gum processing. Fillers suitable for use in the gum base of the preferred embodiment include, but are not limited to, carbonate types such as magnesium and calcium carbonate, ground limestone and silicate types such as magnesium and aluminum silicate, clay, alumina, talc, as well as titanium oxide, mono-, di- and tricalcium phosphate, cellulose polymers such as ethyl, methyl and wood mixtures thereof, and derivatives thereof.

Softeners modify the texture and cause the hydrophobic and hydrophilic components of the base/chewing gum to be miscible. Softeners suitable for use in the inventive gum base of the preferred embodiment include, but are not limited to hydrogenated vegetable oil, nonhydrogenated vegetable oil, lard, hydrogenated tallow, cocoa butter, gylcerol monostearate, glycerol triacetate, lecithin, mono-, di- and triglycerides, acetylated mono-, di- and triglycerides, distilled mono-, di- or triglycerides, fatty acids such as stearic palmitic, oleic, linoleic and linolenic, mixtures thereof, and derivatives thereof.

Waxes aid in the curing of the finished gum made from the gum base as well as improve the release of flavor, shelf-life and texture. Waxes suitable for use within the preferred embodiment of the present invention include, but are not limited to, synthetic waxes such as polyethylene and Fischer-Tropsch waxes, natural waxes such as candelilla, carnauba, beeswax, rice bran, petroleum waxes such as microcrystalline and paraffin, mixtures thereof, and derivatives thereof.

Antioxidants prolong shelf-life and storage of gum base, finished gum or their respective components including fats and flavor oils. Antioxidants suitable for use in gum base of preferred embodiment include, but are not limited to, butylated hydroxyanisole (BHA), butylated hydroxytoluene (BHT), beta-carotenes, tocopherols, acidulants such as Vitamin C, propyl gallate, other synthetic and natural types, mixtures thereof, and derivatives thereof.

Colorants import desired color characteristics or remove undesired color by whitening of the base. Colorants suitable for use in the gum base of the preferred embodiment include, but are not limited to, FD&C type lakes, plant extracts, fruit and vegetable extracts, titanium dioxide, mixtures thereof, and derivatives thereof Gum bases are typically prepared by adding an amount of the elastomer, elastomer solvent and filler to a heated sigma blade mixer with a front to rear speed ratio of typically 2:1. The initial amounts of the ingredients is determined by the working capacity of the mixing kettle in order to attain a proper consistency. After the initial ingredients have massed homogeneously, the balance of the elastomer solvent, filler, softeners, etc. are added in a sequential manner until a completely homogeneous molten mass is attained. This can usually be achieved in one to three hours, depending on the formulation. The final mass temperature can be between about 30° C. to about 133° C., more preferably between about 50° C. to about 100° C., and most preferably between about 60° C. to about 90° C. The completed molten mass is emptied from the mixing kettle into coated or lined pans, extruded or cast into any desirable shape and allowed to cool and solidify.

If an animal-protein or plant-protein based animal digestible elastomer of the preferred embodiment is to be utilized, the processing temperature should be below 100° C., to prevent coacervation of these particular elastomers. The gum base may be comprised almost entirely of the animal digestible elastomer of the preferred embodiment and the other gum base ingredients present in only small quantities to offer different characteristics to the base. Alternatively, the animal digestible elastomer may be modestly present in the gum base while the other base ingredients are present at higher levels to offer somewhat typical gum base characteristics, but modified by the elastomer.

In addition to a water insoluble gum base portion, a typical chewing gum base composition includes a water soluble bulk portion and one or more flavorant, medicinal, or nutritional agents. The water soluble portion can include bulk sweeteners, high intensity sweeteners, flavorants, softeners, emulsifiers, colors, acidulants, fillers, antioxidants, and other components that provide desired attributes.

Softeners are added to the chewing gum in order to optimize the chewability and mouth feel of the gum. The softeners, which are also known as plasticizers and plasticizing agents, generally constitute between approximately 0.5 to about 15% by weight of the chewing gum. The softeners may include glycerin, lecithin, combinations thereof, and derivatives thereof. Aqueous sweetener solutions such as those containing sorbitol, hydrogenated starch hydrolysates, starch hydrolysates combinations thereof, and derivatives thereof may also be used as softeners and binding agents in the chewing gum.

Bulk sweeteners include both sugar and sugarless components. Bulk sweeteners typically constitute 5 to about 95% by weight of the chewing gum, more typically 20 to 80% by weight, and more commonly, 30 to 60% by weight of the chewing gum.

Sugar sweeteners generally include saccharide-containing components commonly known in the chewing gum art, including, but not limited to, sucrose, dextrose, maltose, dextrin, dried invert sugar, fructose, levulose, galactose, corn syrup solids, and derivatives thereof, alone or in combination.

Sorbitol can be used as a sugarless sweetener. Additional sugarless sweeteners can include, but are not limited to, other sugar alcohols such as mannitol, xylitol, hydrogenated starch hydrolysates, maltitol, and derivatives thereof, alone or in combination.

High intensity artificial sweeteners can also be used in combination with the above. Preferred sweeteners include, but are not limited to sucralose, aspartame, salts of acesulfame, alitame, saccharin and its salts, cyclamic acid and its salts, gylcyrrhizin, dihydrochalcones, thaumatin, monellin, and derivatives thereof, alone or in combination. In order to provide longer lasting sweetness and flavor perception, it may be desirable to encapsulate or otherwise control the release of at least a portion of the artificial sweetener. Techniques such as wet granulation, dry granulation, spray drying, spray chilling, fluid bed coating, coacervation, and fiber extension may be used to achieve the desired release characteristics.

Usage level of the artificial sweetener will vary greatly and will depend upon such factors as potency of the sweetener, rate of release, desired sweetness of the product, level and type of flavor used and cost considerations. Thus, the active level of artificial sweetener may vary from 0.02 to about 8%. When carriers used for encapsulation are included, the usage level of the encapsulated sweetener will be proportionately higher.

Combinations of sugar and/or sugarless sweeteners may be used in the animal chewing gum. Additionally, the softener may also provide additional sweetness such as with aqueous sugar or alditol solutions.

If a low calorie gum is desired, a low caloric bulking agent can be used. Examples of low caloric bulking agents include, but are not limited to, polydextrose; oligofrutose; fructooligosaccharide; palatinose oligosaccharide; natural carbohydrate gum hydrolysate; or indigestible dextrins. However, other low calorie bulking agents can be used.

A variety of flavorants can also be used. The flavorant can be used in amounts of approximately 0.1 to about 15 weight percent of the gum, preferably about 0.2 to about 5% weight percent. Flavoring agents may include essential oils, synthetic oils or mixtures thereof including, but not limited to, oils derived from plants and fruits such as citrus oils, fruit essences, peppermint oil, spearmint oil, other mint oils, clove oil, oil of wintergreen, anise and the like. Artificial flavoring agents and components may also be used. Natural and artificial flavoring agents may be combined in any sensorially acceptable fashion. Preferably, the chewing gum composition is flavored with traditional and non-traditional chewing gum flavorants and breath-freshening agents such as fruits (strawberry, melon, and the like), mints, and natural or artificial meat flavors such as beef, chicken, pork, fish, and the like. Thus, the chewing gum composition of the preferred embodiment may be either sweetened or salted.

Of these above-mentioned gum ingredients, the most preferred are simply flavorants such as oil or water soluble types, sweeteners such as polyols, alditols, corn syrup, artificial high-intensity types, and texture modifiers such as water, glycerin, lecithin and the like. The most preferred texture modifier for use with the preferred embodiment of the present invention is glycerin.

By way of example, to make an animal digestible chewing gum comprised of at least one animal digestible animal-protein, plant-protein, or polysaccharide elastomer alone or in combination of the preferred embodiment that entirely replaces a typical gum base, approximately 1 to about 99 percent by weight of the animal digestible elastomers of the preferred embodiment is added to sigma blade mixer. It should be noted that the preferable percent level of the animal digestible elastomer of the preferred embodiment will vary depending on the gum cud size desired. For example, for a small gum cud, the preferred level of elastomer is from approximately 15 to about 30 weight percent and for a large gum cud, from approximately 50 to about 95 weight percent.

In mixing the elastomer within the animal digestible chewing gum composition of the preferred embodiment, the temperature of the mixture should be below 100° C., when an animal or plant-protein is utilized within the composition. Preferably, the temperature of the mixture should be between about 20° C. to about 70° C., and more preferably, between about 25° C. to about 50° C. If an animal or plaint-protein elastomer is not utilized within the preferred embodiment, i.e. polysaccharide elstomer only, then the temperature of the mixture can be between about 70° C. to about 130° C., preferably between about 100° C. to about 120° C.

During the mixing, texture modifiers may then be added to soften and moisten the elastomer of the preferred embodiment if the mixture appears firm or dry. The preferred texturizers are water and glycerin, and the most preferred is glycerin. The level of the modifiers may range from approximately 1 to about 50 percent, depending on the level of animal digestible elastomer used. Preferably, the texturizer level may range from approximately 5 to 40 weight percent and more preferably, from 6 to about 25 weight percent.

Next, the sweeteners may be added and blended into the batch. Usually, the alditol and polyol sweeteners are used as a bulking agent in gum batches having low levels of elastomer, from 15 to 30 weight percent for example. The high intensity sweeteners may be used in combinations. Corn sweeteners and the like may be used in either gum batch.

Typically, the aditol and polyol type bulking sweeteners are added at from about 20 to 80 weight percent and preferably, from 30 to 60 weight percent. The high intensity sweetener may be present from about 0.1 to 3.0 weight percent, more preferably, from 0.5 to 1.5 weight percent.

Next, flavorants are added at a range of from about 0.5 to about 2.0 weight percent. Usually, the water soluble flavorants and the powdered flavorants are used in the gum batch at higher levels than the oil soluble flavorants. The water soluble or oil soluble flavorantss are preferred.

Additional optional ingredients, such as colorants, may be added to the batch.

The resultant chewing gum composition of the present invention will be more digestively acceptable to animals through inclusion of the novel animal digestible elastomers. In addition, the resultant chewing gum composition has the capability of extending the period of time an animal will chew such a composition before subsequent swallowing and ingestion leading to various positive masticatory effects such as enhanced dental hygiene. Lastly, the resultant chewing gum containing the novel animal digestible elastomers are substantially free of parasites and toxic microorganisms, increasing the safety profile for such compositions.

By way of example, and not limitation, examples of the present invention will now be given.

A gum base containing the typical ingredients and novel animal digestible elastomer of the preferred embodiment are described below:

|  | Ex. 1 | Ex. 2 | Ex. 3 | Ex. 4 | Ex. 5 | Ex. 6 | Ex. 7 |
| --- | --- | --- | --- | --- | --- | --- | --- |
| Animal Digestible Elastomer | 10 | 25 | 40 | 50 | 65 | 80 | 90 |
| Synthetic Rubber | 15 | 15 | 10 | 5 | 10 | — | — |
| Vinyl Polymer | 15 | 10 | — | 15 | 10 | 10 | 5 |
| Elastomer Plasticizer | 20 | 20 | 10 | — | — | — | — |
| Filler | 25 | 25 | 20 | 15 | 10 | — | — |
| Softener | 15 | 5 | 5 | 2 | 5 | 5 | 5 |
| Wax | — | — | 15 | 13 | — | 3 | — |

Preferably, the animal digestible elastomer of the preferred embodiment is used directly in the gum making process. More preferably, the elastomer takes the place of the typical base used within the gum making process. Typical gum ingredients can then be blended and then mixed with the elastomer of the preferred embodiment with little difficulty.

The following examples, and not limitations, illustrate other various methods of forming the animal digestible chewing gum composition of the preferred embodiment.

EXAMPLE 1

To a single blade mixture set at 50° C., 300 grams of wheat gluten are added. While the mixture is running, 205 grams of distilled water are slowly added. Following this addition, 0.6 grams of aspartame, 1.8 of potassium sorbate, and 14.6 grams of sorbitol solution (70 percent) are added. All of these ingredients are then mixed for 8 minutes. Then, 12 grams of calcium citrate and 54 grams of high-amylose starch are added. Following an additional 8 minutes of mixing for all of these ingredients, 12 grams of vanilla flavor are then added. The gum is then discharged at 20 minutes, shaped, and cut to 1" by 1" by 0.5" chunks.

EXAMPLE 2

In this particular example, the same ingredients like that of Example 1 are mixed together in the same fashion, but the finished gum chunks are further coated with chocolate to prevent moisture loss and to provide additional flavor.

EXAMPLE 3

In this particular example, the same ingredients and method of mixture of Example 1 are utilized, but 150 grams of wheat gluten is replaced with 150 grams of wheat gliadin to provide for a tougher chew. It should be noted that the rigidity of the animal digestible chewing gum composition of the preferred embodiment can be varied through selection of different animal digestible elastomers alone or in combination with one another. For example, in an alternative embodiment of the present invention, wheat gliadin can be used as a replacement for wheat gluten as the animal digestible elastomer. In doing so, such an elastomer increases the rigidity of the chewing gum composition of the alternative embodiment such that the composition may be shaped into harder chew-toy configurations. Since the novel elastomers of the preferred embodiment are substantially free of parasites and/or microorganisms, chewing gum/chew-toy compositions of the alternative embodiment can be utilized as a safer alternative to natural rawhide animal treats frequently infected with parasites and/or toxic microorganisms. Further, due to the increased rigidity, the chewing gum/chew-toy compositions of the alternative embodiment also provide further enhanced animal dental cleansing.

EXAMPLE 4

In this particular example, the animal digestible chewing gum composition of the preferred embodiment containing the novel animal digestible elastomeris prepared with an enzyme solution. The steps of this particular process include:

Step 1 (Preparation of enzyme solution): A propylene glycol aqueous solution is prepared by mixing PG and water in a ratio of 1:1 by weight. Alkaline Protease Concentrate (APC 3.0 grams) is then added into 280 milliliters of PG aqueous solution.

Step 2 (Preparation of base) To a sigma blade mixer set at 60° C. and 300 rpm, 300 grams of zein and the above APC solution are added. After one hour of mixing, 4 grams of citric acid and 0.4 grams of disodium 5' inosinate are. Then 40 grams of malt powder, 40 grams of maltodextrin, and 80 grams of hydrolyzed gelatin are added and mixed for 40 minutes.

Step 3 (Preparation of gum): The mixer is reset at 37° C. and 60 rpm. Accsulfame K (6 grams) and honeysuckle flavor (6 ml) are added and mixed for 10 minutes before discharge. The enzyme is then deactivated by putting the gum in an oven set at 100° C. for 15 minutes.

Each of these other examples are merely illustrative of the animal digestible elastomers and chewing composition of the preferred embodiment. It should be understood that various changes and modifications of these examples described herein will be apparent to those skilled in art. Such changes in modifications can be made without departing from the scope of the present invention and without diminishing its intended advantages.

Indeed, the animal digestible chewing gum composition of the present invention exhibits a texture and level of elasticity that allows the gum piece to quickly conform to the shapes of an animal's tooth surface upon the first bite. The animal digestible chewing gum composition of the present invention also exhibits a moderate amount of tact to the surfaces to encourage extended chewing times by the animal. Such attributes impede the animals intent to immediately swallow the chewing gum, forcing the animal to chew, while slowly working the gum mass towards the rear of the mouth, where the mass can then be safely swallowed and ingested. Chewing times as long as 1.5 minutes have been observed in animals after administration of a single piece of ingestible chewing gum of the present invention.

Further, because the animal chewing gum of the present invention has the ability to increase the chewing time an animal chews such a composition, flavorants and breath-freshening agents can be added to the composition to aid in improving the animal's breath as well.

Lastly, as a result of the physical and textural properties of the chewing gum composition of the present invention, the composition can be used as a convenient delivery vehicle for medicinal and nutritional agents. The animal digestible chewing gum of the preferred embodiment can be wrapped or placed around medicaments or nutritional compounds in various dosage forms, i.e. pills, such that when an animal readily chews the composition of the present invention and subsequently swallows, the medicinal or nutritional agent is delivered to the animal internally.

In should be understood that various changes or modifications of the present preferred embodiment described herein will be apparent to those skilled in the art. Such changes or modifications can be made without departing from the spirit and scope of the present invention and without diminishing its intended advantages. It is therefore intended that such changes and modifications be covered by the appended claims.

What is claimed is:

1. A method of delivering an agent to an animal comprising the steps of:

providing a chewing gum including the agent, a water soluble gum portion, and a water insoluble gum portion including an animal digestible elastomer; and administering the chewing gum to the animal such that the chewing gum is capable of delivering the agent to the animal when the animal chews the chewing gum.

2. The method of claim 1, wherein the animal digestible elastomer comprises at least one elastomer selected from the group consisting of animal digestible animal protein, plant protein, polysaccharide, and derivatives thereof.

3. The method of claim 1, wherein the agent is delivered to the animal as the chewing gum is chewed by the animal.

4. The method of claim 1, wherein the agent is delivered to the animal as the chewing gum is digested by the animal.

5. The method of claim 1, wherein the agent is a pill.

6. The method of claim 1, wherein the agent is wrapped within the chewing gum.

7. The method of claim 1, wherein the agent is selected from the group consisting of a medicament, a nutritional agent, a flavorant, and a breath-freshening agent.

8. The method of claim 1, wherein the chewing gum is capable of inducing an extended chewing time as compared to a gum that does not include an animal digestible elastomer.

9. A method of providing dental hygiene to an animal comprising the steps of:

providing a chewing gum that includes a water soluble gum portion and a water insoluble gum portion including an animal digestible elastomer;

administering the chewing gum to the animal; and causing the chewing gum to stick and conform to the animal's teeth during chewing such that the animal is required to chew the chewing gum over an extended period of time as compared to a gum without the animal digestible elastomer.

10. The method of claim 9, wherein the animal digestible elastomer comprises at least one elastomer selected from the group consisting of animal digestible animal protein, plant protein, polysaccharide, and derivatives thereof.

11. The method of claim 9, wherein the chewing gum further comprises at least one component selected from the group consisting of a medicament, a nutritional agent, a breath-freshening agent, and a flavorant.

* * * * *